United States Patent
Klingenberg et al.

(10) Patent No.: US 7,312,452 B2
(45) Date of Patent: Dec. 25, 2007

(54) MOBILE REMOTE DETECTION DEVICE AND REMOTE DETECTION METHOD FOR METHANE GAS ACCUMULATIONS

(75) Inventors: Hans H. Klingenberg, Tuebingen (DE); Andreas Fix, Gilching (DE); Peter Mahnke, Stuttgart (DE); Christian Lemmerz, Stadtbergen (DE)

(73) Assignee: Deutsches Zentrum fur Luft- und Raumfahrt E.V., Bonn (DE)

( * ) Notice: Subject to any disclaimer, the term of this patent is extended or adjusted under 35 U.S.C. 154(b) by 0 days.

(21) Appl. No.: 11/256,560

(22) Filed: Oct. 21, 2005

(65) Prior Publication Data

US 2006/0114464 A1 Jun. 1, 2006

Related U.S. Application Data

(63) Continuation of application No. PCT/EP04/04048, filed on Apr. 16, 2004.

(30) Foreign Application Priority Data

Apr. 24, 2003 (DE) ................................ 103 19 560

(51) Int. Cl.
*G01N 21/00* (2006.01)

(52) U.S. Cl. ............... 250/339.13; 250/339.11; 250/339.12; 250/338.5; 356/437

(58) Field of Classification Search ........... 250/339.03, 250/339.11, 339.12, 339.13, 338.5; 356/437, 356/438
See application file for complete search history.

(56) References Cited

U.S. PATENT DOCUMENTS 3,783,403 A * 1/1974 Hook et al. .................. 372/12

(Continued)

FOREIGN PATENT DOCUMENTS

EP 0 489 546 A2 6/1992

(Continued)

OTHER PUBLICATIONS

Klingenberg et al. "Wavelength Switching in the Acceptance Bandwidth of a Dual Injection Seeded Optical Parametric Oscillator". Proceedings of the SPIE, vol. 5481, No. 1 (Mar. 2004), pp. 108-114.*

(Continued)

*Primary Examiner*—David Porta
*Assistant Examiner*—Mark R Gaworecki
(74) *Attorney, Agent, or Firm*—Alston & Bird LLP

(57) ABSTRACT

The invention relates to a mobile remote detection device for accumulations of methane, comprising an emitter device having a light source in order to generate light, the wavelength of said light source being tuned with the spectral signature of methane, whereby the light can be directed onto a measuring field. The detection device also comprises a detector device for detecting backscattered light, and an evaluation device. The aim of the invention is to improve the remote detection device in such a manner that it has a high degree of measuring sensitivity with a compact and stable structure. According to the invention, the light source generates light with a wavelength at which methane is absorbed, wherein the wavelength lies between 3200 nm and 3300 nm, and the light source has an optical parametric oscillator with injection seeding, the oscillator being associated with a pump laser.

21 Claims, 4 Drawing Sheets

U.S. PATENT DOCUMENTS

| | | | |
|---|---|---|---|
| 4,489,239 A * | 12/1984 | Grant et al. | 250/339.03 |
| 4,555,627 A | 11/1985 | McRae, Jr. | |
| 4,560,270 A * | 12/1985 | Wiklund et al. | 356/5.1 |
| 4,874,572 A * | 10/1989 | Nelson et al. | 376/256 |
| 5,117,126 A | 5/1992 | Geiger | |
| 5,343,483 A * | 8/1994 | Farrell et al. | 372/10 |
| 5,377,219 A | 12/1994 | Geiger | |
| 5,742,053 A | 4/1998 | Rekunyk | |
| 5,757,624 A | 5/1998 | Kawaguchi | |
| 5,892,586 A * | 4/1999 | Thony et al. | 356/437 |
| 5,946,095 A * | 8/1999 | Henningsen et al. | 356/519 |
| 6,166,934 A | 12/2000 | Kajouke et al. | |
| 6,258,082 B1 * | 7/2001 | Lin | 606/5 |
| 6,340,848 B1 | 1/2002 | Maeda | |
| 6,690,472 B2 | 2/2004 | Kulp et al. | |
| 6,763,261 B2 * | 7/2004 | Casscells et al. | 600/474 |
| 6,809,870 B2 * | 10/2004 | Fohl et al. | 359/627 |
| 6,822,742 B1 * | 11/2004 | Kalayeh et al. | 356/437 |
| 6,838,671 B2 * | 1/2005 | Compana et al. | 250/349 |
| 6,842,534 B1 | 1/2005 | Paz-Pujalt et al. | |
| 6,897,465 B2 * | 5/2005 | Remillard et al. | 250/559.38 |
| 7,026,600 B2 * | 4/2006 | Jamieson et al. | 250/221 |
| 2004/0088113 A1 | 5/2004 | Spoonhower et al. | |

FOREIGN PATENT DOCUMENTS

| | | |
|---|---|---|
| EP | 1 193 470 A3 | 4/2002 |
| EP | 1 416 258 A1 | 5/2004 |
| GB | 2 311 852 A | 10/1997 |

OTHER PUBLICATIONS

Robinson et al. "DIAL Measurements for Air Pollution and Fugitive-Loss Monitoring". Proceedings of the SPIE, vol. 2506 (Sep. 1995), pp. 140-149.*

Anderson, S. G., "Remote Sensing," *Laser Focus World*, 1995, pp. 1-2, vol. 31 (12).

Baumgartner, R. A. and R. L. Byer, "Continuously Tunable Ir Lidar with Applications to Remote Measurements of $SO_2$ and $CH_4$," *Applied Optics*, 1978, pp. 3555-3561, vol. 17 (22).

Demtröder, W. (1998) *Laser Spectroscopy: Basic Concepts and Instrumentation* ($2^{nd}$ ed., Springer-Verlag, Berlin).

Filippov, P. G., et al., "A Helicopter Complex for Inspecting the Linear Part of Main Gas Pipelines and Ecological Monitoring of Oil and Gas Facilities," *Applied Energy: Russian Journal of Fuel, Power, and Heat Systems*, 1997, pp. 1-21, vol. 35 (1).

Fix, A., "Investigation of the Spectral Properties of Optical Parametric Oscillators Based on the Nonlinear Optical Material β-Barium Borate," Universität Kaiserslautern, Verlag Schaker Aachen, 1995, Abstract only.

Ikuta, K., et al., "Differential Absorption Lidar at 1.67 μm for Remote Sensing of Methane Leakage," *Jpn. J. Appl. Phys.*, 1999, pp. 110-114, vol. 38, Part 1 (1A).

Kabanov, M. V., et al., "Monitoring of Antropogenic and Natural Methane Emissions," Second International Methane Mitigation Conference, 2000.

Karapuzikov, A. I., et al., "Feasibility of Applying a Tunable $TEA-CO_2$-Laser-Based Helicopter-Borne Lidar to Detection of Methane Leakages," *Atmos. Oceanic Opt.*, 1999, pp. 350-357, vol. 12 (4).

Karapuzikov, A. I., et al., "Modeling of Helicopter-Borne Tunable $TEA\ CO_2$ DIAL System Employment for Detection of Methane and Ammonia Leakages," *Infrared Physics & Technology*, 2000, pp. 87-96, vol. 41.

Karapuzikov, A. I., et al., "Tunable TEA $CO_2$ Laser for Long-Range DIAL Lidar," *Infrared Physics & Technology*, 2000, pp. 77-85, vol. 41.

Lancaster, D. G. and J. M. Dawes, "Methane Detection with a Narrow-Band Source at 3.4 μm Based on a Nd:YAG Pump Laser and a Combination of Stimulated Raman Scattering and Difference Frequency Mixing," *Applied Optics*, 1996, pp. 4041-4045, vol. 35 (21).

Lee, S. W., et al., "Methane Concentration Measurements with a Mid-Infrared Optical Parametric Oscillator-Based Differential Absorption Lidar System," *CLEO*, 1999, pp. 272-273, Pacific Rim '99.

Lee, S. W., et al. (1998) "An OPO-Based Lidar System for Differential Absorption Measurements of Methane in the 3 μm Region," *Nineteenth International Laser Radar Conference*, ed. SINGH, et al. (National Aeronautics and Space Administration: Hampton).

Mahnke, P., et al., "Fast Tuning of External-Cavity Diode Lasers," *Applied Optics*, 2002, pp. 6380-6384, vol. 41 (30).

Menyuk, N. and D. K. Killinger, "Atmospheric Remote Sensing of Water Vapor, HCl and $CH_4$ Using a Continuously Tunable $Co:MgF_2$ Laser," *Applied Optics*, 1987, pp. 3061-3065, vol. 26 (15).

Milton, M. J. T., et al., "Injection-Seeded Optical Parametric Oscillator for Range-Resolved DIAL Measurements of Atmosphere Methane," *Optics Communications*, 1997, pp. 153-160, vol. 142.

Murray, E. R., et al., "Remote Measurement of HCl, $CH_4$, and $N_2O$ Using a Single-Ended Chemical-Laser Lidar System," *Applied Optics*, 1976, pp. 3140-3148, vol. 15 (12).

Philippov, P. G., et al., "DIAL—Infrared Lidar for Monitoring of Main Pipelines and Gas Industry Objects," *SPIE*, 1998, pp. 119-127, vol. 3504.

Prasad, N. S. and A. R. Geiger, "Remote Sensing of Propane and Methane by Means of a Differential Absorption Lidar by Topographic Reflection," *Opt. Eng.*, 1996, pp. 1105-1111, vol. 35 (4).

Uthe, E. E. and N. B. Nielsen, "Small-Aircraft Atmospheric Lidar Techniques," Second International Airborne Remote Sensing Conference and Exhibition, Jun. 1996, pp. I-11-I-20.

Velikanov, S. D., et al., "DF Laser Application for Hydrocarbon Control in the Atmosphere," *SPIE*, 1998, pp. 231-236, vol. 3493.

Walmsley, H. L. and S. J. O'Connor, "The Accuracy and Sensitivity of Infrared Differential Absorption Lidar Measurements of Hydrocarbon Emissions from Process Units," *Pure Appl. Opt.*, 1998, pp. 907-925, vol. 7.

Walmsley H. L., et al., "The Application of DIAL Remote Sensing Technology to Safety and Environmental Monitoring," International Gas Research Conference, 1995, pp. 1135-1142.

Walmsley, H. L. and S. J. O'Connor, "The Measurement of Atmospheric Emissions from Process Units Using Differential Absorption LIDAR," *SPIE*, 1997, pp. 60-71, vol. 3104.

White, K. O. and W. R. Watkins, "Erbium Laser as a Remote Sensor of Methane," *Applied Optics*, 1975, pp. 2812-2813, vol. 14 (12).

Zirnig, W., et al., "A Concept for Natural Gas Transmission Pipeline Monitoring Based on New High-Resolution Remote Sensing Technologies," International Gas Research Conference, 2001.

Zirnig, W., et al., "Überwachung von Erdgastransportleitungen," *Gas Wasser Abwasser*, 2002, No. 5, Abstract only.

Zirnig, W. L., et al., "High-Resolution Remote Sensing Used to Monitor Natural Gas Pipelines," *Earth Observation Magazine*, Feb. 13, 2003, pp. 1-9.

* cited by examiner

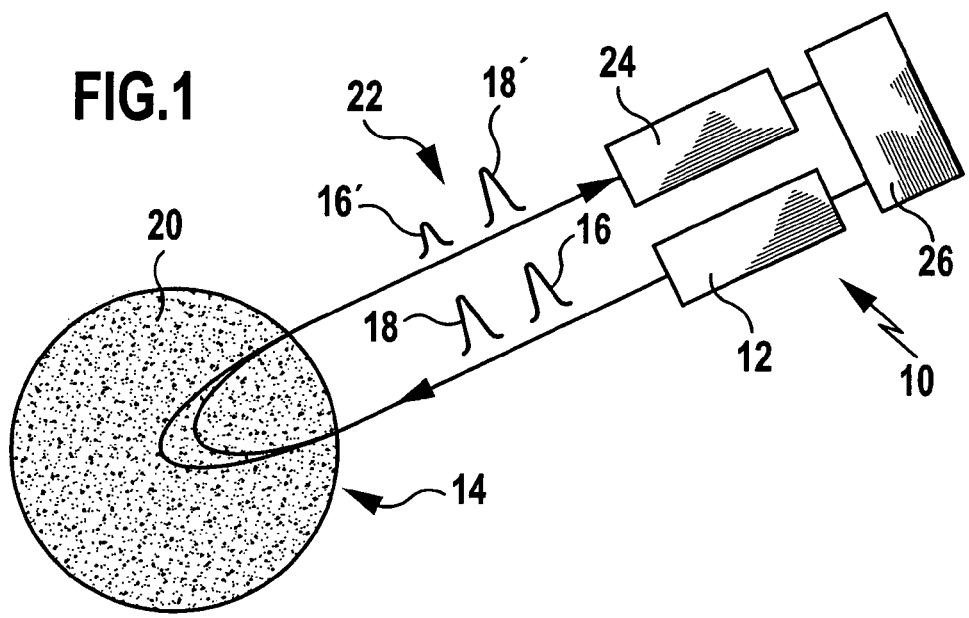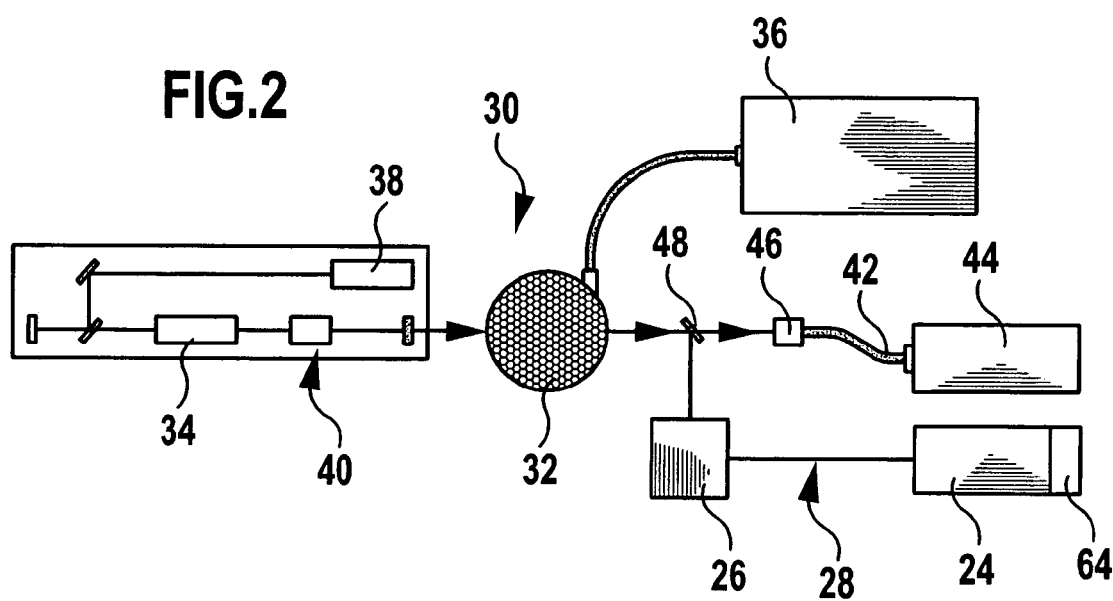

MOBILE REMOTE DETECTION DEVICE AND REMOTE DETECTION METHOD FOR METHANE GAS ACCUMULATIONS

CROSS REFERENCE TO RELATED APPLICATIONS

This application is a continuation of international application PCT/EP2004/004048, filed on Apr. 16, 2004, and also claims the benefit of German Application No. 103 19 560.2, filed Apr. 24, 2003, both of which are incorporated herein by reference in their entirety and for all purposes.

BACKGROUND OF THE INVENTION

1. Field of the Invention

The invention relates to a mobile remote detection device for methane gas accumulations, comprising an emitter device with a light source to generate light, the wavelength of which is tuned with the spectral signature of methane, wherein the light can be directed towards a measuring field, a detector device for the detection of backscattered light, and an evaluation device. The invention additionally relates to a remote detection method for methane gas accumulations in which light pulses are directed onto a measuring field, the wavelength of which is tuned with the spectral signature of methane, and backscattered light is detected.

2. Description of Related Art

Remote detection devices are described in the article "Überwachung von Erdgas-transportleitungen" ["Monitoring of natural gas transport pipelines"] by W. Zimig et al. in Gas Wasser Abwasser, No. 5, 2002, pages 337-344. The method described in the article is also referred to as LIDAR (light detection and ranging). Natural gas pipelines can be monitored for leaks with such a system, which is carried in particular by an aircraft.

SUMMARY OF THE INVENTION

In accordance with one aspect of the invention, a mobile remote detection device is provided with a high degree of measuring sensitivity in association with a compact and stable structure. The light source of the mobile remote detection device generates light with a wavelength at which methane absorbs, wherein the wavelength lies between 3200 nm and 3300 nm, and the light source comprises an optical parametric oscillator with injection seeding, which is associated with a pump laser. The pump laser can be operated in injection seeding mode. The light source can be of stable and compact structure, and therefore it can also be used on an aircraft, in which typically varying temperatures are present and also mechanical effects such as vibrations are present.

Because light is generated with a wavelength matched to a specific methane absorption line and lying in the range of between 3200 nm and 3300 nm, a high sensitivity is assured. Moreover, by selecting a wavelength from the above wavelength range, it is assured that the backscattered light can be properly detected. In particular, InAs detectors can be used, since the corresponding wavelength lies below the band edge of InAs. Moreover, such detectors can then also be cooled to obtain a high signal-to-noise ratio and thus in turn increase the measuring sensitivity.

To obtain a high measuring sensitivity, it is necessary that light pulses of high intensity with narrow spectral width are generated. Because according to the invention a seeded optical parametric oscillator and a seeded pump laser are provided, the light source can be operated on narrow band, wherein it is tunable.

In certain embodiments, the light source emits light with the wavelength of 3240 nm or 3220 nm or 3249 nm or 3270 nm or 3290 nm. These wavelengths correspond to methane absorption lines, wherein a high measuring sensitivity can be achieved. With these lines, there is also a low cross-sensitivity to atmospheric water vapor. The wavelength of 3240 nm has proved particularly advantageous. Cooled InAs detectors can then be used for the detector device in order to obtain a good signal-to-noise ratio with high efficiency.

It is favorable if a seed source of the optical parametric oscillator generates light with a seed wavelength of $\lambda_s^{-1} = \lambda_p^{-1} - \lambda_i^{-1}$, wherein $\lambda_p$ is the wavelength of th laser of the optical parametric oscillator and $\lambda_i$ is a methane absorption wavelength. In particular, $\lambda_i$ is the idler wavelength. This results in the advantage that on the basis of the above-mentioned wavelength range, seed wavelengths can lie in the range of 1600 nm. In this wavelength range, which is of interest for telecommunications, there exist high-quality narrow-band diode lasers with DBR or DFB structure or with an external resonator. Existing diode lasers can then be used as seed sources for the optical parametric oscillator.

It is favorable if the optical parametric oscillator is coupled to an optical emitter system by means of a fiber optic light guide. As a result, the light source and the optical emitter system can be spatially separated, so that the light source can be arranged in an internal area of a helicopter, for example, while the optical emitter system can be mounted on the outside of the helicopter. This in turn provides a simple possibility with respect to a rigid spatial coupling of the direction of emission or the emitter device and the viewing direction of the detector device. This also allows a mechanical decoupling to be achieved between the light source and optical emitter system, so that the effect of temperature fluctuations, vibrations and similar can be reduced. It is most particularly advantageous if the fiber optic light guide comprises sapphire fibers. At the relevant wavelengths sapphire fibers have a high transmission with a high optical destruction threshold.

It has proved advantageous if the pump laser is a Q-switched solid state laser, such as an Nd:YAG laser, for example. Narrow-band transmission light of the desired wavelength can be generated by means of such a pump laser.

It is most particularly advantageous if the light source provides light of a first wavelength corresponding to a methane absorption line and reference light of a second wavelength outside an absorption line. The reference light allows the measurement of methane gas distributions even of low concentration (trace gas distributions). The absorption properties of the methane to be detected is utilized by applying the Beer-Lambert absorption law. The effects of the atmosphere and the backscatter onto the measured signal can be eliminated via the reference light pulse. The corresponding method is also referred to as DIAL (differential absorption LIDAR).

It is favorable when a light pulse sequence can be generated. The light pulse sequence has a specific repetition rate. The higher the repetition rate, the greater the ability to monitor a measuring field such as a pipeline, for example, continuously during a movement of the carrier. For example, for a helicopter-mounted remote detection device, a repetition rate in the light pulse sequence in the order of magnitude of 100 Hz is provided.

It is necessary that the time interval between an absorption light pulse with an absorption wavelength and a reference light pulse with a non-absorption wavelength is selected so that, taking into consideration a movement speed of a carrier for the device, there is a spatial overlap between the measuring field illuminated by the absorption light pulse and the measuring field illuminated by a reference light pulse separated in time. This ensures that the absorption light pulse and the associated reference light pulse scan the same measuring field and thus the reference light pulse can indeed act as reference.

It is favorable if the interval between the absorption light pulse and the reference light pulse is less than 300 μs. Such a system can be advantageously used on an aircraft such as a helicopter. At a typical traveling speed of 100 km/h of the aircraft, this moves less than 1 cm in 300 μs. Therefore, with appropriate adjustment of the time interval, it is assured that substantially the same measuring field is illuminated and detection of the backscattered light pulses is also permitted.

It is most particularly advantageous if the pulse laser for the optical parametric oscillator can be operated in a double-pulse mode. In principle, it is possible that separate pump lasers are provided for the absorption light pulses and for the reference light pulses. If the pump laser allows a double-pulse mode, then one pump laser is sufficient. The device can then be compact in structure and operated in an energy efficient manner, and therefore it is particularly suitable for use with an aircraft.

The pulse laser is diode-pumped, for example, wherein to generate double pulses a Q-switching circuit can be switched at least twice during a diode pump pulse. In this way, the optical parametric oscillator can be pulsed with a double-pulse, which in turn results in the transmission light of the optical parametric oscillator comprising a double-pulse in the emitted light pulse sequence. In this case, the first light pulse is the absorption light pulse and the second light pulse is the reference light pulse or vice versa.

It is favorable if the light source is tunable in a wavelength range of approximately 3240 nm. A high measuring sensitivity can be achieved if the spectral width of the light generated by the light source is smaller than the line width of the corresponding methane absorption line.

A detector of the detector device is preferably cooled, so that a high signal-to-noise ratio is present. In particular, the detector is thermoelectrically cooled, for example, by means of one or more Peltier elements. As a result, no coolant such as nitrogen needs to be transported with the device.

A high measuring sensitivity is achieved if the detector device comprises one or more InAs detectors. The band edge of InAs lies at approximately 3300 nm. A high yield (efficiency) is achieved as a result of the wavelength being selected according to the invention to below this band edge for the absorption light pulses. With InAs detectors, a good efficiency can also be achieved without nitrogen cooling. For example, cooling down to a temperature of approximately −40° C. is achieved thermoelectrically. As a result, the device can be constructed with a compact structure.

For focusing the received light, the detector device can comprise a telescope. It is also possible that a Fresnel lens is provided for focusing. Fresnel lenses have the advantage that they are light, inexpensive and allow a shorter structural length for the optical receiver system of the detection device. These advantages are particularly relevant for a mobile remote detection device. There exist materials that have a high transmission within the relevant wavelength ranges.

It is most particularly advantageous if a distance-measuring system is provided. Such a distance-measuring system allows a column of the natural methane background to be detected. As a result, the measured signal can then be corrected to thus in turn obtain a high measuring sensitivity. It is possible, in principle, to provide a separate distance-measuring system, which comprises a laser range finder, for example. However, it is most particularly advantageous if a time-resolved measurement is provided with respect to the transit time of light pulses between emission and receipt of reflection light pulses. As a result, the distance measurement is automatically conducted precisely at the location at which the methane gas measurement is also conducted.

The device according to the invention is provided for assembly on an aircraft and in particular on a helicopter.

Further, in accordance with a further aspect of the invention, a method is provided with which a high degree of measuring sensitivity can be achieved. In accordance with an embodiment of the invention, the wavelength lies at 3240 nm or 3220 nm or 3249 nm or 3270 nm or 3290 nm, and the transmission light is generated by means of a seeded optical parametric oscillator, which is pumped by a pump laser. The pump laser can be seeded. The remote detection method for methane gas accumulations according to the invention has the advantages already outlined in association with the device according to the invention.

Further advantageous configurations have likewise already been outlined in association with the device according to the invention. The following description of preferred embodiments serves to explain the invention in more detail in association with the drawing.

BRIEF DESCRIPTION OF THE DRAWINGS

In order to assist the understanding of embodiments of the invention, reference will now be made to the appended drawings, which are not necessarily drawn to scale, and wherein:

FIG. 1 is a schematic view of a remote detection device for gas accumulations for explanation of the LIDAR method and the DIAL method;

FIG. 2 is a schematic block diagram of an embodiment of a remote detection device according to the invention;

DETAILED DESCRIPTION OF THE INVENTION

Figure 3:
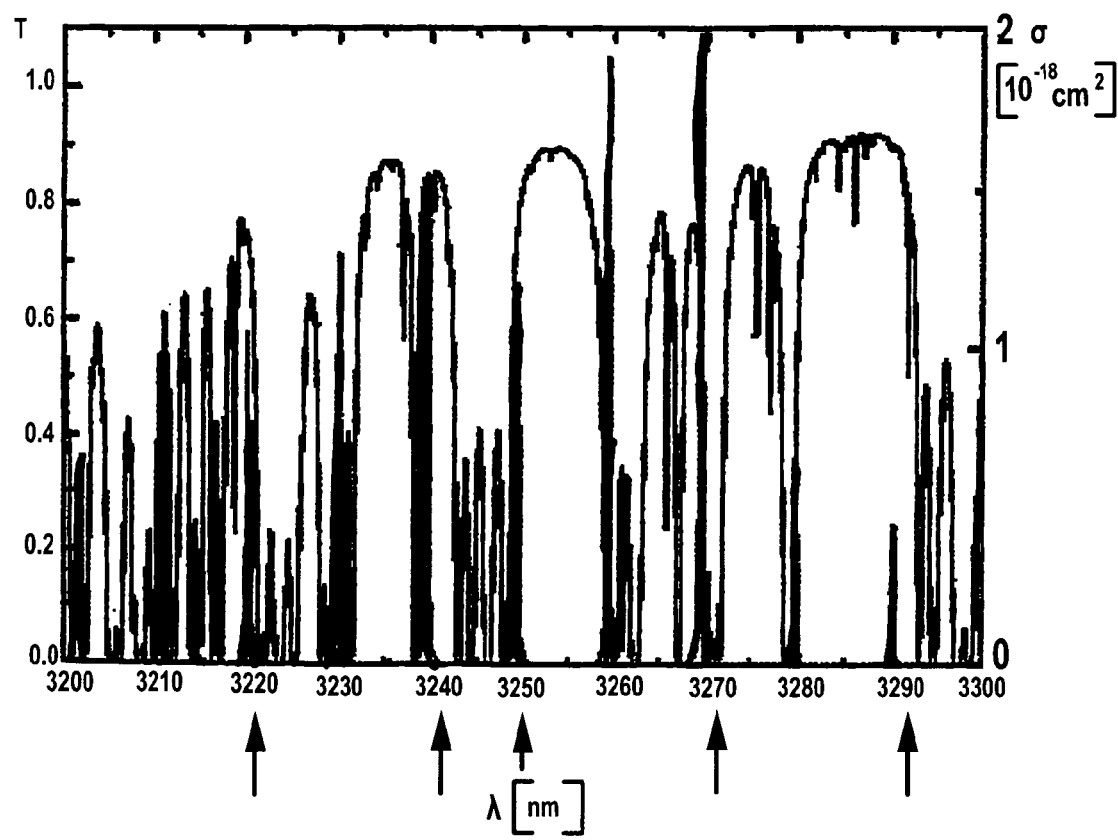
FIG. 3 shows the calculated transmission of atmospheric water vapor in a standard atmosphere at a path length of 300 m in the wavelength range between 3200 nm and 3300 nm (left scale) and the absorption cross-section of methane in this wavelength range (right scale), wherein the usable absorption wavelengths are indicated by arrows.

The present invention now will be described more fully hereinafter. However, this invention may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural referents unless the context clearly dictates otherwise.

A remote detection device according to the invention, which is shown schematically in FIG. 1 and is given the overall reference number 10, comprises an emitter device 12 for laser light with a corresponding optical emitter system, through which the light can be directed onto a measuring field 14.

As will be described in more detail below, the emitter device 12 comprises a light source, which emits laser light pulses 16, 18. In this case, the wavelength of these light pulses 16, 18 is tuned to the spectral signature of the gas to be detected, methane in the case of the present invention. Light 22 backscattered by a methane gas accumulation 20 is detected by a detector device 24 with an optical receiver system. There is provided for evaluation an evaluation device 26, which is in connection to the emitter device 12 and in particular to a control device of the emitter device 12 and assures analysis of the measurement results. In this case, the detector device 24 is rigidly coupled relative to the direction of the transmission light emitted by the emitter device 12. Such an active optical tracking method based on laser light, wherein backscattered light is detected and analyzed, is also referred to as the LIDAR method (LIDAR—light detection and ranging).

In the case of the DIAL method (differential absorption LIDAR), the absorption properties of the gas to be detected are used by application of the Beer-Lambert absorption law. Light pulses 16, 18 of different wavelengths are emitted: the light pulse 16, which is also referred to as on-line pulse, has a wavelength corresponding to an absorption wavelength of the gas to be detected. The corresponding light is absorbed by the gas. In contrast, the light pulse 18 emitted at a staggered time has a wavelength at which the light is not absorbed. The light pulse 18 is also referred to as off-line light pulse. It serves as reference pulse. The reference pulse can also be emitted before the absorption pulse. The LIDAR method and the DIAL method are described in association with atmospheric measurements in Section 15.2.2 in W. Demtröder, Laser Spectroscopy, Corrected Printing, 1998, Springer-Verlag, which is incorporated by reference herein in its entirety.

If gas to be detected is present in the measuring field 14, then back-reflected light 16', which originates from the light pulse 16, is attenuated in comparison to the transmission light pulse 16 because of absorption in the gas accumulation 20. In contrast, a back-reflected reference light pulse 18' is attenuated to a much lesser degree. The product of gas concentration and absorption cross-section can be determined by an intensity comparison.

An embodiment of a remote detection device according to the invention, which is given the overall reference 28 in FIG. 2, comprises a light source 30, in particular a laser light source, as part of the emitter device 12. The light source 30 comprises an optical parametric oscillator 32 (OPO). An OPO is a nonlinear optical system, with which frequency-varying radiation can be continuously generated. An OPO comprises a suitable optical nonlinear medium such as a nonlinear crystal, for example, which is arranged in an optical resonator. The OPO is pumped by means of a pump laser 34. The interaction between the radiation of the coherent pumping field of the pump laser 34 and the nonlinear susceptibility of the crystal, for example, generates two frequency-varying waves. These are referred to as signal wave and idler wave.

The wavelengths are determined by energy conservation and momentum conservation in the form of a phase matching condition. The frequency variability is obtained by a suitable change in the phase matching condition. Suitable optical crystals are, for example, $LiNbO_3$, KTP, KTA, $KNbO_3$ or materials with quasi-phase matching.

The OPO is seeded via a seed laser 36. In injection seeding, narrow-band coherent radiation of an external light source (seed source) is coupled into the OPO 32. This is a known method, which is described, for example, in the publication of A. Fix, "Untersuchung der spektralen Eigenschaften von optischen parametrischen Oszillatoren aus dem optisch nicht linearen Material Betabariumborat" ["Examination of the spectral properties of optical parametric oscillators of the optically nonlinear material beta barium borate"], thesis, Kaiserslautern University, Verlag Schaker, Aachen, 1995, which is incorporated by reference herein in its entirety.

Seeding enables the line width of a pulsed OPO to be reduced without the losses in the OPO resonator being greatly increased. The efficiency of the OPO is not reduced by seeding, wherein the narrow line width can be achieved with a simple structure. With regard to the seed source, there are only few requirements for its radiation intensity. The seed source 36 must be tunable for a tunable OPO.

The pump laser 34 for the OPO is preferably a Q-switched solid state laser such as an Nd:YAG laser, for example. It is provided according to the invention that the pump laser 34 is also seeded and comprises a seed laser as seed source 38 for this purpose. The pump laser 34 supplies pump pulses in order to generate the light pulses 16, 18. In principle, two different pump lasers can be provided to generate the on-line pulses 16 and the off-line pulses 18.

A single pump laser 34, which permits a double-pulse mode, is provided according to the invention. For example, a Q-switching mode 40 of the pump laser, which comprises a Pockels cell, for example, is configured for this such that pump pulses can be generated at a time interval, and these then generate the light pulses 16, 18 in the OPO 32.

For example, the pump laser 34 is diode-pumped with a diode pump pulse with a length of 400 µs, for example. During such a diode pump pulse the Q-switching circuit is switched twice in order to generate two pump pulses of the pump laser 34, which are then coupled into the OPO 32. For example, the Q-switching circuit is operated at a time interval of 200 µs in order to generate pulses that are accordingly separated in time. The pump pulses of the pump laser 34 have the same wavelength.

By providing a single pump laser 34, which allows a double-pulse mode of operation, the device 28 can be constructed to be more compact, since no second pump laser needs to be provided. Moreover, the current consumption of the device can be reduced, precisely because no second pump laser is present.

The OPO 32 is temporally switched over in keeping with the pump pulses of the pump laser 34 in order to generate the on-line pulses and off-line pulses of different wavelength. For example, the seed laser 36 is switched in an appropriately controlled manner for this purpose, i.e., the OPO is seeded with seed light of different wavelength for the generation of absorption light and reference light.

The light generated by the OPO 32, i.e. the light pulses 16, 18, which are generated in a light pulse sequence, is transmitted to an optical emitter system 44 via a fiber optic light guide 42. The laser light (i.e., the light pulse sequence with the light pulses 16, 18) can be directed onto the measuring field 14 by means of the optical emitter system 44.

The light source 30 can be spatially separated from the optical emitter system 44 by the fiber optic light guide 42. If the device 28 is carried by a helicopter, for example, this enables the light source 30 to be arranged in the helicopter, while the optical emitter system 44 can be mounted on the helicopter as an external load. Thus, the mechanical requirements for assembly on the helicopter can be reduced. In this case, it must also be taken into consideration that the detector device 24 for backscattered light must be arranged in the vicinity of the optical emitter system 44.

Sapphire fibers are particularly suitable for the fiber optic light guide 42 with the wavelengths explained in more detail below. The appropriate fiber optic light guide 42 has a high transmission with high optical destruction threshold. This allows the transmission light of the light source 30 to be coupled in without defects.

A beam splitter 48 is arranged between the OPO 32 and a coupling point 46 for coupling laser light into the fiber optic light guide 42. This enables a component beam of the light coupled out by the OPO 32 to be directed to the evaluation device 26 to provide a reference for the transmission light for the analysis of the backscattered light 22.

It is provided according to the invention that the on-line wavelength of the light pulses 16 corresponds to an absorption wavelength of methane, wherein this wavelength lies between 3200 nm and 3300 nm. A methane absorption spectrum is shown in FIG. 3. The absorption lines in this range, which have a low cross-sensitivity to water vapor, are marked via arrows. The line, which is used according to the invention, lies at 3239.7 nm or 3220.1 nm or 3249.4 nm or 3269.5 nm or 3290.2 nm. At these wavelengths the transmission of atmospheric water vapor is relatively high, and therefore there is a low cross-sensitivity to water vapor. It is expected that with an on-line wavelength of 3239.7 nm for a device carried by helicopter, methane can be detected from 80 m to 140 m with discharge rates of 10 to 200 l/h.

For the on-line wavelengths in accordance with the above given data, there exist appropriate detectors, via which backscattered light 22 can be detected with sufficient sensitivity. Peltier-cooled InAs detectors can be used in particular. These are efficient and low-noise. The band edge of InAs lies in the vicinity of 3300 nm. High efficiency is assured as result of absorption lines below 3300 nm being selected.

The band edge of InAs detectors shifts to lower wavelengths with lower temperatures. The noise of the detector is reduced at lower temperatures. At the wavelength of 3239.7 nm, a high efficiency is obtained with slight low noise, since the detector can be cooled (e.g., thermoelectrically by means of Peltier cooling), wherein a sufficient distance from the band edge is maintained.

The off-line wavelength lies in the vicinity of the corresponding on-line wavelength, wherein it must lie outside an absorption line. It is advantageous if there is a high differential absorption in comparison to the on-line wavelength.

The light source 30 according to the invention enables on-line light pulses 16 with one of the above-mentioned wavelengths and corresponding off-line light pulses 18 to be generated. It is advantageous if the light pulse with the on-line wavelength is generated on the idler wavelength $\lambda_i$ and the seeding is conducted on the signal wavelength $\lambda_s$. The following relation then applies for the signal wavelength: $\lambda_s^{-1} = \lambda_p^{-1} - \lambda_i^{-1}$, wherein $\lambda_p$ is the wavelength of the pump laser 34. With this method, the seed wavelength lies in the range of 1600 nm. In the corresponding wavelength range there exist high-quality narrow-band diode lasers with DBR structure or DFB structure or with an external resonator, and therefore the structural expenditure for the seed laser 36 is minimized. In this case, narrow-band laser light of high intensity can be generated. A measuring sensitivity of 50 ppm×m or better can be achieved.

Figure 4:
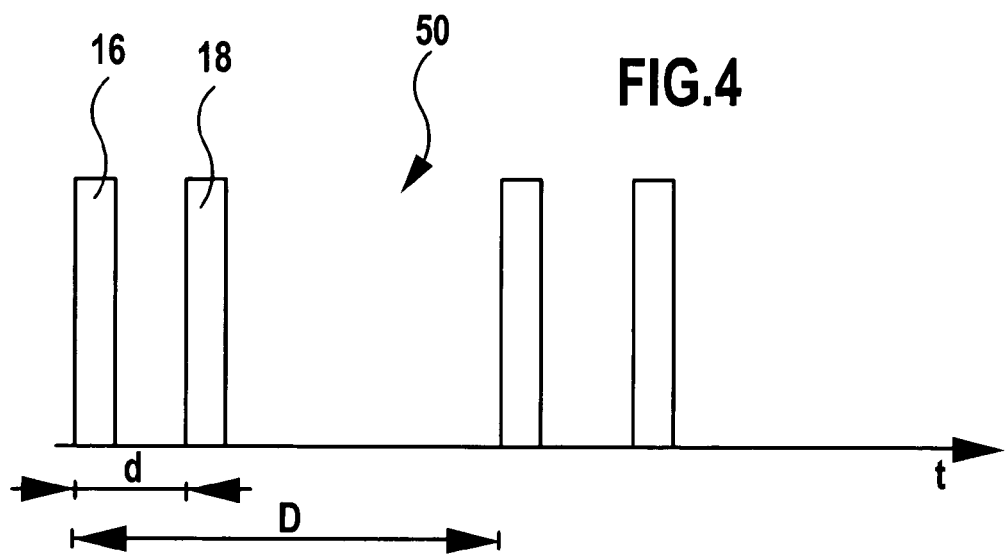
FIG. 4 is a schematic view of the time pulse curve of the transmission light.

A light pulse sequence 50 is shown schematically in FIG. 4. In this case, a time interval d between an on-line light pulse 16 and an off-line light pulse 18 is determined on the basis that an impingement area of the measuring field 14 of each of the two light pulses 16, 18 should overlap and should overlap as far as possible. If a carrier of the device 28 is mobile, such as a helicopter, for example, flying over a natural gas pipeline, then the light pulses 16, 18 impinge on different spatial areas. The light pulses 18' can no longer serve as reference pulses if they originate from an impingement area that is different from the impingement area of the light pulses 16.

An advantageous time interval between the light pulses 16, 18 lies in the order of magnitude of 200 μs to 300 μs. For example, if a helicopter moves at a speed of 100 km/h, then in a time of 300 μs, this helicopter advances by a distance of approximately 1 cm. With such a distance, an adequate overlap is also assured with respect to the detector device 24.

An interval D of the on-line pulses 16 in the light pulse sequence 50 typically lies in the order of magnitude of 10 ms, which corresponds to a repetition rate of 100 Hz. If the helicopter flies at a speed of 100 km/h, for example, then in 10 ms it advances approximately 30 cm. Therefore, a repetition rate of 100 Hz assures that a measuring field along the flight route of the helicopter, e.g. along a pipeline route, can be covered virtually completely.

Figure 5:
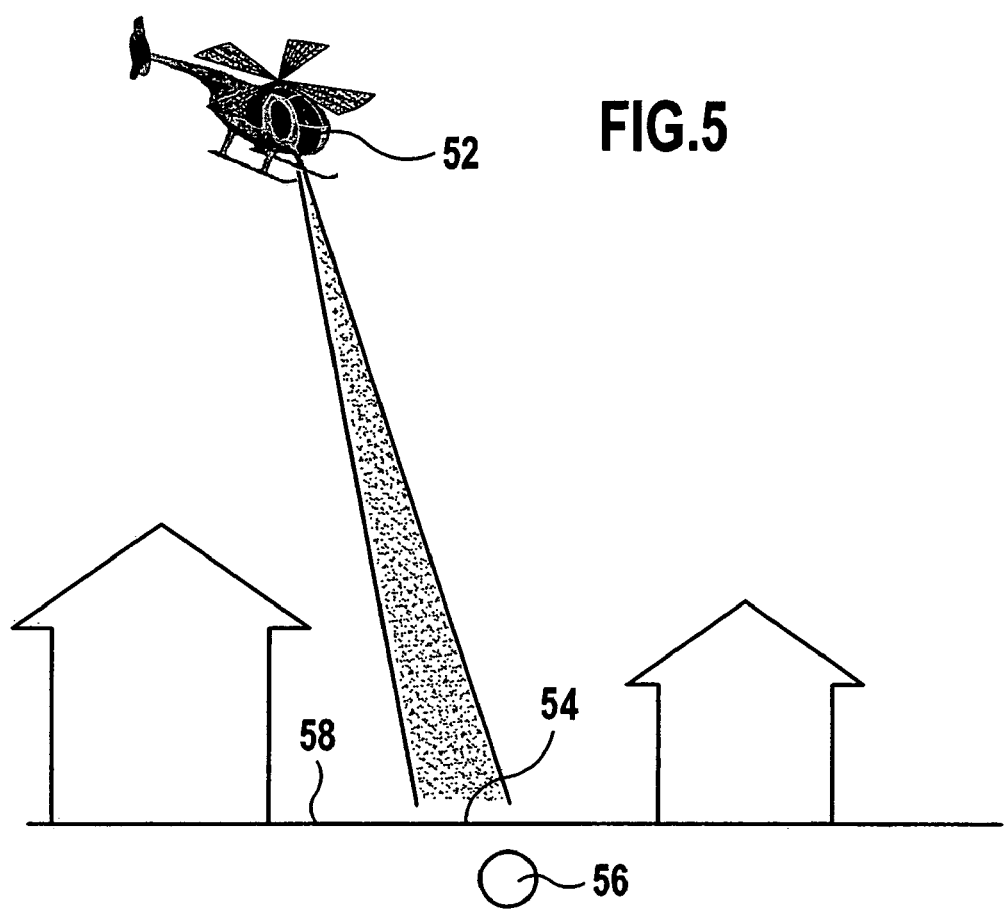
FIG. 5 is a schematic view of an example of use for the device according to the invention.

A helicopter 52 is schematically shown in FIG. 5 as an aircraft that carries the remote detection device 28 according to the invention. The helicopter 52 flies along a pipeline route 54 with one or more natural gas pipelines 56. Methane gas accumulations 20 can be formed above the natural gas pipeline 56 as a result of leaks therein. The optical emitter system 44 directs the transmission light in a transmission beam onto the pipeline route 54 and the detector device 24 receives the backscattered light 22.

It is provided according to the invention that a distance measurement is conducted. As a result of this, the natural methane background is determined in its effect on the measurement result and the measurement result can be corrected accordingly. The column of the natural methane background in the impingement area of the measuring field 14 can be determined via a distance measurement. It is possible, in principle, to provide a separate distance-measuring system such as a laser range finder, for example. It is also possible to perform a distance determination via a navigation system in association with pre-stored terrain models.

A distance-measuring system is provided according to the invention which measures the light pulses reflected by the ground 58 (FIG. 5) in a time-resolved manner. A receiver system is provided which is integrated into the detector device 24, which has such a band width that the reflected pulses can be time-resolved. In this case, the distance measurement is performed automatically according to the invention at the location, at which measurement is also being performed with respect to a methane accumulation 20.

Figure 6:
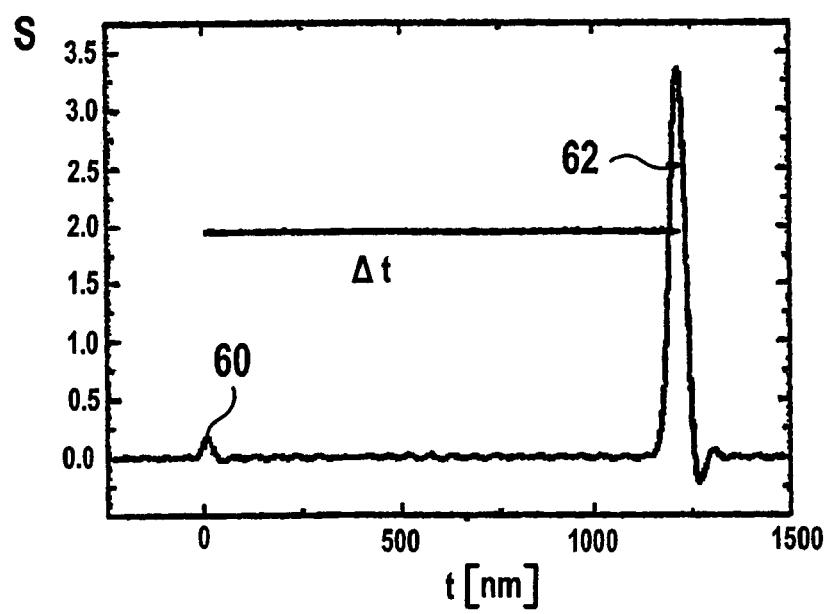
FIG. 6 shows the time sequence of pulses for distance measurement.

A corresponding time sequence graph is shown in FIG. 6: a near field signal 60 triggers the distance measurement. This near field signal 60 is received via the transmission light 16, for example, wherein a coupling out occurs via the beam splitter 48.

The evaluation device 26 then determines the time period At until a back-reflected ground signal 62 arrives. The distance can then be determined from this time difference. In the embodiment shown in FIG. 6, the transit time amounts to 1204 ns, from which results a distance of 180 m between the optical emitter system 44 and the ground 58.

Figure 7:
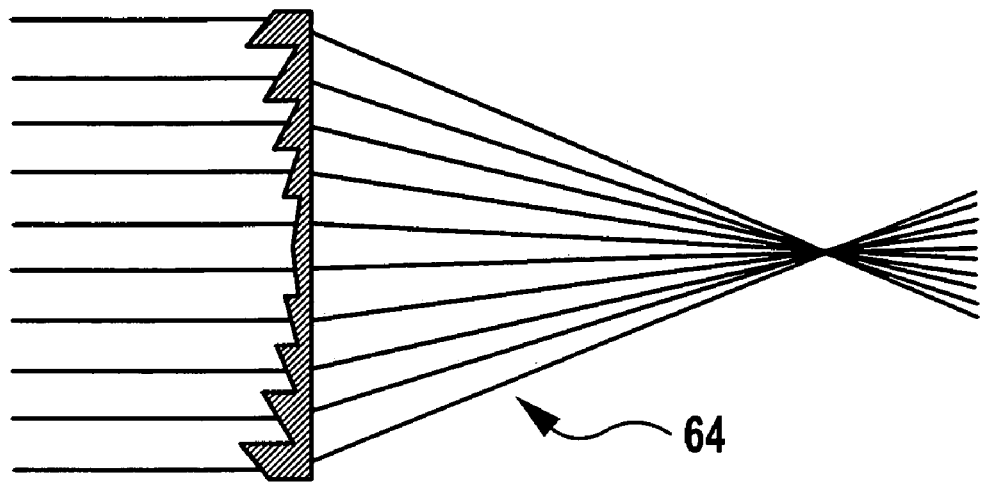
FIG. 7 is a schematic view of a Fresnel lens.

The detector device 24 can include a telescope, for example, for focusing the received light. A Fresnel lens 64 can also be provided for focusing. Such a Fresnel lens is shown schematically in FIG. 7. It has a refractive structure, which is configured so that a focusing effect arises for traversing light. Fresnel lenses have advantages over telescopes in that they are lighter, less expensive to produce, and allow shorter structural lengths for the optical receiver system of the detector device 24. These advantages are very relevant in the case of a mobile, in particular aircraft-assisted, use of the remote detection device 28 according to the invention.

In the wavelength range between 3200 nm and 3300 nm, the solar background is smaller by approximately two orders of magnitude than in the visible spectral range. As a result, in contrast to the visible spectral range, a good signal-to-noise ratio, also taking into consideration the solar background, is obtained for a Fresnel lens.

Figure 8:
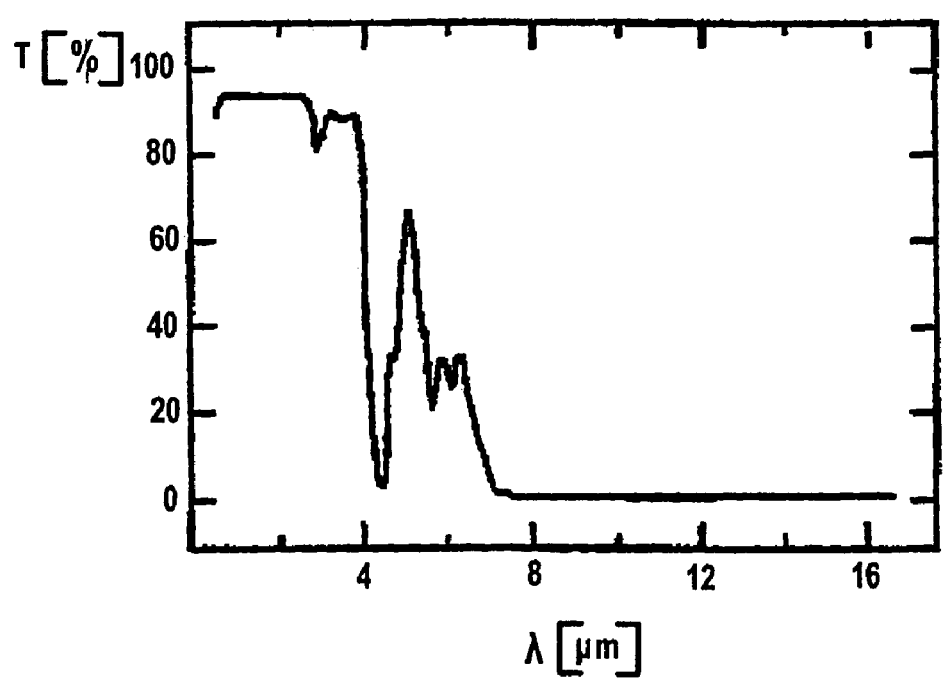
FIG. 8 shows the transmission of the material, POLY IR® 5 (infrared-transmitting plastic material available from Fresnel Technologies, Inc.), as material for a Fresnel lens as a function of the wavelength.

There exist materials that have a sufficiently high transmission in the relevant spectral range of between 3200 nm and 3300 nm. FIG. 8 shows the transmission as a function of the wavelength for the material POLY IR® 5 (infrared-transmitting plastic material available from Fresnel Technologies, Inc.) by way of example. It can be seen that the transmission lies below 4000 nm at approximately 90%. A Fresnel lens 64, which is made from such a material, is suitable for focusing the backscattered light 22.

As a result of the remote detection device 28 according to the invention, a laser system is provided that can be constructed to be stable and compact, and produced at favorable cost. It allows a high measuring sensitivity of better than 50 ppm×m in a single shot to be obtained. The remote detection device 28 according to the invention can be used in an aircraft such as a helicopter, for example. With respect to the illumination of the measuring field by the light pulses 16 and the reference light pulses 18 via a double-pulse operation, an adequate surface overlap is obtained at a typical traveling speed of a helicopter. A pipeline route can be monitored spatially continuously.

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A mobile remote detection device for methane gas accumulations, comprising:
    an emitter device with a light source to generate light, the wavelength of which is tuned with the spectral signature of methane, wherein the light is directable onto a measuring field;
    wherein the light source provides a light pulse of a first wavelength corresponding to a methane absorption line and a reference light pulse of a second wavelength outside an absorption line;
    wherein the interval between the absorption light pulse and the reference light pulse is less than 300 μs;
    a detection device comprising a detector adapted for detecting backscattered light; and
    an evaluation device;
    wherein the light source generates light with a wavelength at which methane absorbs, wherein the wavelength lies between 3200 nm and 3300 nm;
    wherein the light source comprises an optical parametric oscillator with injection seeding, which is associated with a single pump laser;
    wherein the pump laser is operable in a double-pulse mode;
    wherein the device is adapted for assembly on an aircraft; and
    wherein the optical parametric oscillator is coupled to an optical emitter system by means of a fiber optic light guide.

2. The mobile remote detection device according to claim 1, wherein the light source emits light at the wavelength of 3240 nm or 3220 nm or 3249 nm or 3270 nm or 3290 nm.

3. The mobile remote detection device according to claim 1, wherein a seed source of the optical parametric oscillator generates light with a seed wavelength of $\lambda_s^{-1} = \lambda_p^{-1} - \lambda_i^{-1}$, wherein $\lambda_p$ is the wavelength of the pump laser of the optical parametric oscillator and $\lambda_i$ is a methane absorption wavelength.

4. The mobile remote detection device according to claim 3, wherein $\lambda_i$ is an idler wavelength.

5. The mobile remote detection device according to claim 1, wherein the fiber optic light guide comprises sapphire fibers.

6. The mobile remote detection device according to claim 1, wherein the pump laser is a Q-switched solid state laser.

7. The mobile remote detection device according to claim 1, wherein the device is configured to generate a light pulse sequence.

8. The mobile remote detection device according to claim 7, wherein the time interval between an absorption light pulse with an absorption wavelength and a reference light pulse with a non-absorption wavelength is selected so that, taking a movement speed of a carrier for the device into consideration, there is a spatial overlap between the measuring field illuminated by the absorption light pulse and the measuring field illuminated by the reference light pulse.

9. The mobile remote detection device according to claim 1, wherein the pump laser is diode-pumped, wherein to generate double pulses a Q-switching circuit is switchable at least twice during a diode pump pulse.

10. The mobile remote detection device according to claim 1, wherein the light source is tunable in a wavelength range of about 3240 nm.

11. The mobile remote detection device according to claim 1, wherein the spectral width of the light generated by the light source is substantially narrower than the line width of the corresponding methane absorption line.

12. The mobile remote detection device according to claim 1, wherein the detector is cooled.

13. The mobile remote detection device according to claim 12, wherein the detector is cooled thermoelectrically.

14. The mobile remote detection device according to claim 1, wherein the detection device comprises one or more InAs detectors.

15. The mobile remote detection device according to claim 1, wherein the detection device comprises a telescope.

16. The mobile remote detection device according to claim 1, wherein the detection device comprises a Fresnel lens for focusing.

17. The mobile remote detection device according to claim 1, further comprising a distance-measuring system.

18. The mobile remote detection device according to claim 1, wherein the device is configured to provide a time-resolved measurement with respect to the transit time of light pulses between emission and receipt of corresponding reflection light pulses.

19. The mobile remote detection device according to claim 1, wherein the pump laser is operated in injection seeding mode.

20. A remote detection method for methane gas accumulations, comprising:
   directing absorption light pulses from an aircraft onto a measuring field;
   tuning the wavelength of the absorption light pulses with the spectral signature of methane; and
   detecting backscattered light at the aircraft;
   wherein the wavelength of the absorption light pulses lies at 3240 nm or 3220 nm or 3249 nm or 3270 nm or 3290 nm, and wherein the light pulses are generated by means of a seeded optical parametric oscillator, which is pumped by a single pump laser;
   wherein a reference light pulse with a non-absorption wavelength is emitted at an interval from the absorption light pulse;
   wherein the pump laser is operated in a double-pulse mode for absorption light pulses and reference light pulses; and
   wherein the optical parametric oscillator is coupled to an optical emitter system by means of a fiber optic light guide.

21. The method according to claim 20, wherein the pump laser is seeded.

* * * * *